(12) United States Patent
Dadd et al.

(10) Patent No.: US 8,447,409 B2
(45) Date of Patent: May 21, 2013

(54) ELECTRONEURAL INTERFACE FOR A MEDICAL IMPLANT

(75) Inventors: Fysh Dadd, Lane Cove (AU); Jim Patrick, Roseville (AU)

(73) Assignee: Cochlear Limited, Macquarie University, NSW (AU)

( * ) Notice: Subject to any disclaimer, the term of this patent is extended or adjusted under 35 U.S.C. 154(b) by 133 days.

(21) Appl. No.: 12/580,045

(22) Filed: Oct. 15, 2009

(65) Prior Publication Data
US 2010/0094380 A1 Apr. 15, 2010

(30) Foreign Application Priority Data
Oct. 15, 2008 (AU) ................................ 2008905362

(51) Int. Cl.
*A61N 1/00* (2006.01)
(52) U.S. Cl.
USPC ........ 607/50; 607/2; 607/51; 607/52; 607/55; 607/56; 607/57
(58) Field of Classification Search
USPC ...................... 607/2, 50–52, 55–57
See application file for complete search history.

(56) References Cited

U.S. PATENT DOCUMENTS

| | | | |
|---|---|---|---|
| 4,919,140 A * | 4/1990 | Borgens et al. | ................. 607/50 |
| 6,156,728 A | 12/2000 | Gao | |
| 6,593,290 B1 | 7/2003 | Gao | |
| 6,653,279 B1 | 11/2003 | Gao | |
| 6,927,204 B2 | 8/2005 | Gao | |
| 2001/0012625 A1 | 8/2001 | Presta et al. | |
| 2002/0006916 A1 | 1/2002 | Song et al. | |
| 2002/0054874 A1 | 5/2002 | Clary et al. | |
| 2002/0110837 A1 | 8/2002 | Chao et al. | |
| 2002/0137893 A1 | 9/2002 | Burton et al. | |
| 2002/0142990 A1 | 10/2002 | Song et al. | |
| 2003/0040082 A1 | 2/2003 | Tuszynski et al. | |
| 2003/0049244 A1 | 3/2003 | Seifer et al. | |
| 2003/0113901 A1 | 6/2003 | Hirst et al. | |
| 2003/0121064 A1 | 6/2003 | Logan et al. | |
| 2003/0134820 A1 | 7/2003 | Song et al. | |
| 2003/0134821 A1 | 7/2003 | Song et al. | |
| 2003/0229134 A1 | 12/2003 | Filbin et al. | |

(Continued)

FOREIGN PATENT DOCUMENTS
WO 98/19700 5/1998

OTHER PUBLICATIONS

Hinkle et al., "The Directions of Growth of Differentiating Neurones and Myoblasts from Frog Embryos in an Applied Electric Field," J. Physiol (1981), 314 pp. 121-135.

(Continued)

*Primary Examiner* — Niketa Patel
*Assistant Examiner* — William Levicky
(74) *Attorney, Agent, or Firm* — Kilpatrick, Townsend & Stockton, LLP.

(57) ABSTRACT

Embodiments are generally directed to improving the interface between one or more electrode contacts of a medical implant and the neurons of a recipient of the medical implant. In an embodiment, a growth factor is applied to stimulate the growth of peripheral processes (also referred to as dendrites). Then an electric field is applied to direct the growth of the peripheral processes towards the electrode contact. Growing peripheral processes towards the electrode contacts may reduce the charge required to stimulate the peripheral processes and improve operation of the medical implant.

26 Claims, 10 Drawing Sheets

U.S. PATENT DOCUMENTS

| | | | |
|---|---|---|---|
| 2003/0232759 | A1 | 12/2003 | Gao |
| 2004/0022790 | A1 | 2/2004 | Schachner |
| 2004/0082516 | A1 | 4/2004 | Tessier-Lavigne et al. |
| 2004/0102375 | A1 | 5/2004 | Lanier et al. |
| 2004/0109860 | A1 | 6/2004 | Clary et al. |
| 2004/0138431 | A1 | 7/2004 | Burton et al. |
| 2004/0186052 | A1 | 9/2004 | Iyer et al. |
| 2004/0224394 | A1 | 11/2004 | Katz et al. |
| 2004/0230231 | A1* | 11/2004 | Thacker et al. .................. 607/5 |
| 2004/0230254 | A1* | 11/2004 | Harrison et al. ................ 607/57 |
| 2005/0187595 | A1 | 8/2005 | Streeter |
| 2006/0088884 | A1 | 4/2006 | Seifer et al. |
| 2006/0089709 | A1 | 4/2006 | Helmus |
| 2006/0270838 | A1 | 11/2006 | Urfer et al. |
| 2006/0287689 | A1* | 12/2006 | Debruyne et al. .............. 607/57 |
| 2007/0067002 | A1 | 3/2007 | Lozano |
| 2007/0203390 | A1 | 8/2007 | Rohan et al. |
| 2007/0264195 | A1 | 11/2007 | Nykiaer et al. |

OTHER PUBLICATIONS

McCaig et al., "Neurotrophins Enhance Electric Field-Directed Growth Cone Guidance and Directed Nerve Branching," Developmental Dynamics 217:299-308 (2000), 10 pages total.

McCaig et al., "Controlling Cell Behavior Electrically: Current Views and Future Potential," Physiol Rev 85: 2005, pp. 943-978.

Prasad et al., "Patterned Live Neural Networks by Induced Electrical Fields for Bio-Sensing," Journal of the Association for Laboratory Automation. University of California, vol. 8 , pp. 81-85, Apr. 1 2003.

Pettingill et al. "Neurotrophic factors and neural prostheses: potential clinical applications based upon findings in the auditory system." IEEE Trans Biomed Eng. Jun. 2007;54(6 Pt 1):1138-48.

Gillespie et al. "Clinical application of neurotrophic factors: the potential for primary auditory neuron protection." Eur J Neurosci. Nov. 2004;22(9):2123-33.

McCaig et al. "Electrical fields, nerve growth and nerve regeneration." Exp. Physiol. 76: 473-494, 1991.

English et al. "Electrical stimulation promotes peripheral axon regeneration by enhanced neuronal neurotrophin signaling." J.Neurobiol. Jan. 31, 2006. pp. 1-15.

Shepherd et al. "Chronic depolarization enhances the trophic effects of brain-derived neurotrophic factor in rescuing auditory neurons following a sensorineural hearing loss." JCompNeurol. 30, 145-158 (2005).

Shepherd et al. "Neurotrophins and electrical stimulation for protection and repair of spiral ganglion neurons following sensorineural hearing loss." Hear Res. Aug. 2008; 242(1-2): 100-109.

Singh et al. "Activity regulates positive and negative neurotrophin-derived signals to determine axon competition." Neuron, vol. 45, 837-845, Mar. 24, 2005.

Goldberg et al. "Retinal ganglion cells do not extend axons by default: promotion by neurotrophic signaling and electrical activity." Neuron vol. 33, 689-702, Feb. 28, 2002.

Sarah L. McGuinness et al., "Exogenous BDNF Rescues Rat Spiral Ganglion Neurons in Vivo", Otology & Neurotology 26: 1064-1072, 2005, 9 pages.

Abstracts of Hearing Preservation Workshop VI, Antwerp Oct. 19-20, 2007, 40 pages.

L. N. Pettingill et al., "Schwann Cells Genetically Modified to Express Neurotrophins Promote Spiral Ganglion Neuron Survival in Vitro", Neuroscience 152 (2008) 821-828, 8 pages.

Robert K. Shepherd et al., "A multichannel scala tympani electrode array incorporating a drug delivery system for chronic intracochlear infusion", Hearing Research 172 (2002) 92-98, 7 pages.

* cited by examiner

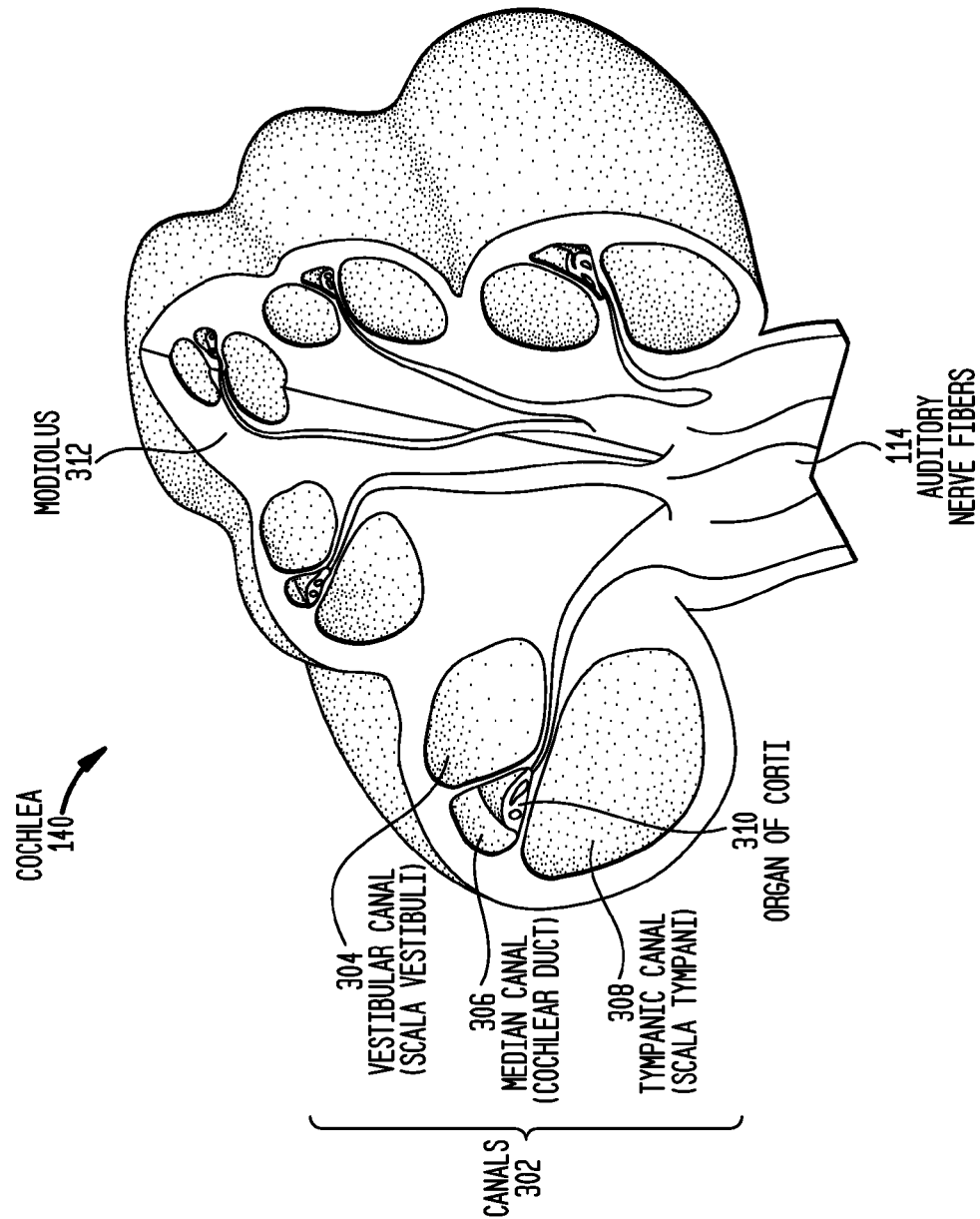

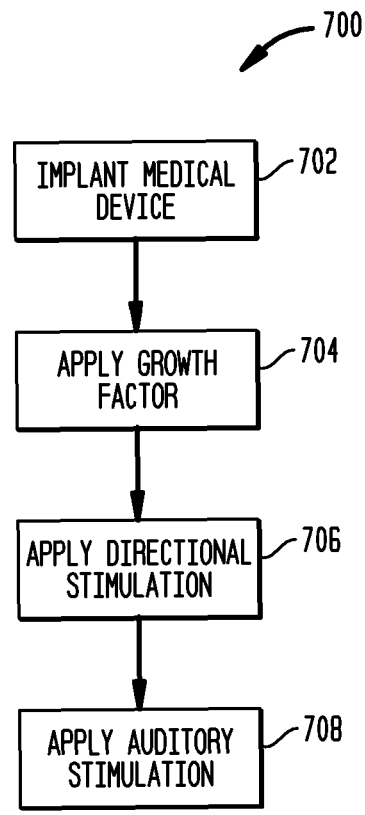
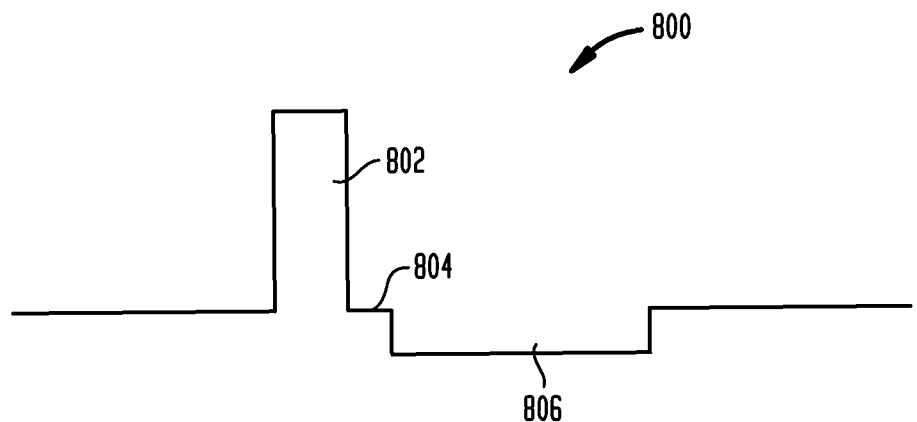

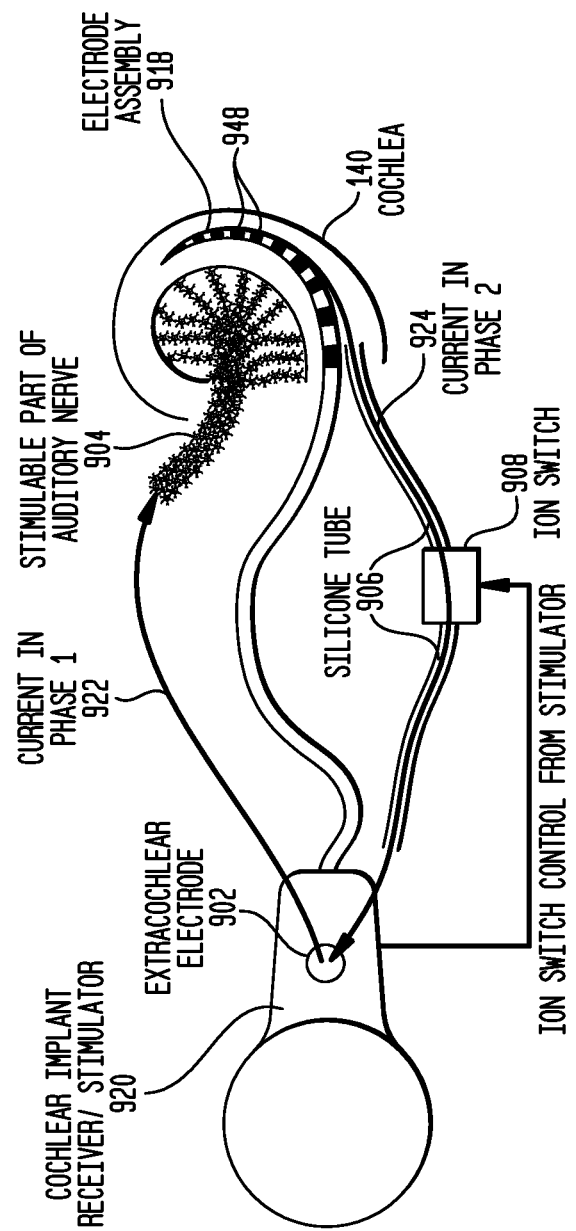

ELECTRONEURAL INTERFACE FOR A MEDICAL IMPLANT

CROSS-REFERENCE TO RELATED APPLICATIONS

The present application claims the benefit of Australian Provisional Patent Application 2008905362; filed 15 Oct. 2008, which is hereby incorporated by reference herein.

BACKGROUND

1. Field of the Invention

The present invention relates generally to medical devices, and more particularly, to improving an interface between electrode contacts of an implantable medical device and the neurons of a recipient.

2. Related Art

Medical devices having one or more implantable components, generally referred to as implantable medical devices, have provided a wide range of therapeutic benefits to patients over recent decades. Implantable hearing prostheses that treat the hearing loss of a prosthesis recipient are one particular type of implantable medical devices that are widely used today.

Hearing loss, which may be due to many different causes, is generally of two types, conductive and sensorineural. In some cases, individuals suffer from hearing loss of both types. Conductive hearing loss occurs when the normal mechanical pathways for sound to reach the cochlea, and thus the sensory hair cells therein, are impeded, for example, by damage to the ossicles. Individuals who suffer from conductive hearing loss typically have some form of residual hearing because the hair cells in the cochlea are undamaged. As a result, individuals suffering from conductive hearing loss typically receive an implantable hearing prosthesis, such as an acoustic hearing aid, middle ear implant, etc., that generates mechanical motion of the cochlea fluid.

In many people who are profoundly deaf, however, the reason for their deafness is sensorineural hearing loss. Sensorineural hearing loss occurs when there is damage to the inner ear, or to the nerve pathways from the inner ear to the brain. As such, those suffering from some forms of sensorineural hearing loss are thus unable to derive suitable benefit from hearing prostheses that generate mechanical motion of the cochlea fluid. As a result, implantable hearing prostheses that deliver electrical stimulation to nerve cells of the recipient's auditory system have been developed. As used herein, the recipient's auditory system includes all sensory system components used to perceive a sound signal, such as hearing sensation receptors, neural pathways, including the auditory nerve and spiral ganglion, and parts of the brain used to sense sounds. Electrically-stimulating hearing prostheses include, but are not limited to, auditory brain stimulators and cochlear prostheses (commonly referred to as cochlear prosthetic devices, cochlear implants, cochlear devices, and the like; simply "cochlear implants" herein.)

In a normal ear, auditory nerve fibers are connected to spiral ganglion cells, which in turn are connected to peripheral processes (also referred to as dendrites), which in turn are connected to hair cells inside the Organ of Corti in the cochlea. Oftentimes sensorineural hearing loss is due to the absence or destruction of the cochlear hair cells which transduce acoustic signals into nerve impulses that are detected by the peripheral processes. Further, the loss of hair cells also eventually results in the loss of peripheral processes.

Cochlear implants generally use an electrode assembly implanted in the cochlea to deliver electrical stimulation signals directly to the spiral ganglion cells thereby bypassing absent or defective hair cells. The electrode contacts of the stimulating assembly differentially activate spiral ganglion cells that normally encode differential pitches of sound.

SUMMARY

In one aspect of the present invention, a method for directing the growth of neural peripheral processes. The method comprises applying to a plurality of neurons a growth factor which promotes growth of the peripheral processes by the neurons, and applying to the neurons an electric field having characteristics which encourage the growth of the peripheral processes in a desired direction.

In another aspect of the present invention, a system for directing the growth of neural peripheral processes. This system comprises a stimulating lead assembly comprising one or more electrode contacts, wherein the stimulating lead assembly is configured to apply a growth factor to promote the growth of peripheral processes by a plurality of neurons; a sound processor configured to generate one or more stimulation data signals; and a stimulator unit configured to applying an electric field to a cochlea of a recipient in accordance with the one or more stimulation data signals, wherein the electric field has characteristics which encourage the growth of the peripheral processes in a desired direction.

In yet another aspect, there is a system for directing the growth of neural peripheral processes. This system comprises a means for applying to a plurality of neurons a growth factor which promotes the growth of peripheral processes by the neurons; and means for applying to the neurons an electric field having characteristics which encourage the growth of the peripheral processes in a desired direction.

BRIEF DESCRIPTION OF THE DRAWINGS

Embodiments of the present invention are described below with reference to the attached drawings, in which:

FIG. 3A is a perspective, partially cut-away view of a cochlea exposing the canals of the cochlea;

FIG. 7 is a flow chart of a method for encouraging the growth of peripheral processes, in accordance with an embodiment of the present invention;

FIG. 8 is an illustration of an exemplary stimulation waveform for directing the growth of peripheral processes, in accordance with an embodiment of the present invention;

FIG. 9B is conceptual diagram illustrating the current flow in different phases of the embodiment of FIG. 9A, in accordance with an embodiment of the present invention.

DETAILED DESCRIPTION

Aspects of the present invention are generally directed to improving the interface between one or more electrode contacts of an implantable medical device and the neurons of a recipient of the medical device. In an embodiment, a growth factor is applied to stimulate the growth of the peripheral processes or dendrites of the neurons. An electric field is applied either subsequent to or concurrent with the application of the growth factor to direct the growth of the peripheral processes towards the electrode contact. Growing peripheral processes towards the electrode contacts may reduce the charge require to stimulate the peripheral processes and thus improve performance of the medical device.

Embodiments of the present invention are described herein primarily in connection with one type of medical device, a hearing prosthesis, namely a cochlear prosthesis (commonly referred to as cochlear prosthetic devices, cochlear implants, cochlear devices, and the like; simply "cochlear implants" herein.) Cochlear implants deliver electrical stimulation to the cochlea of a recipient. As used herein, cochlear implants also include hearing prostheses that deliver electrical stimulation in combination with other types of stimulation, such as acoustic or mechanical stimulation. Although the present embodiments are described with reference to a hearing prosthesis, other embodiments may be used in connection with other medical devices employing an electroneural interface, such as brain stem implants, cortical implants, midbrain implants, pain management devices, ladder control devices, and breathing control devices, etc.

Figure 1:
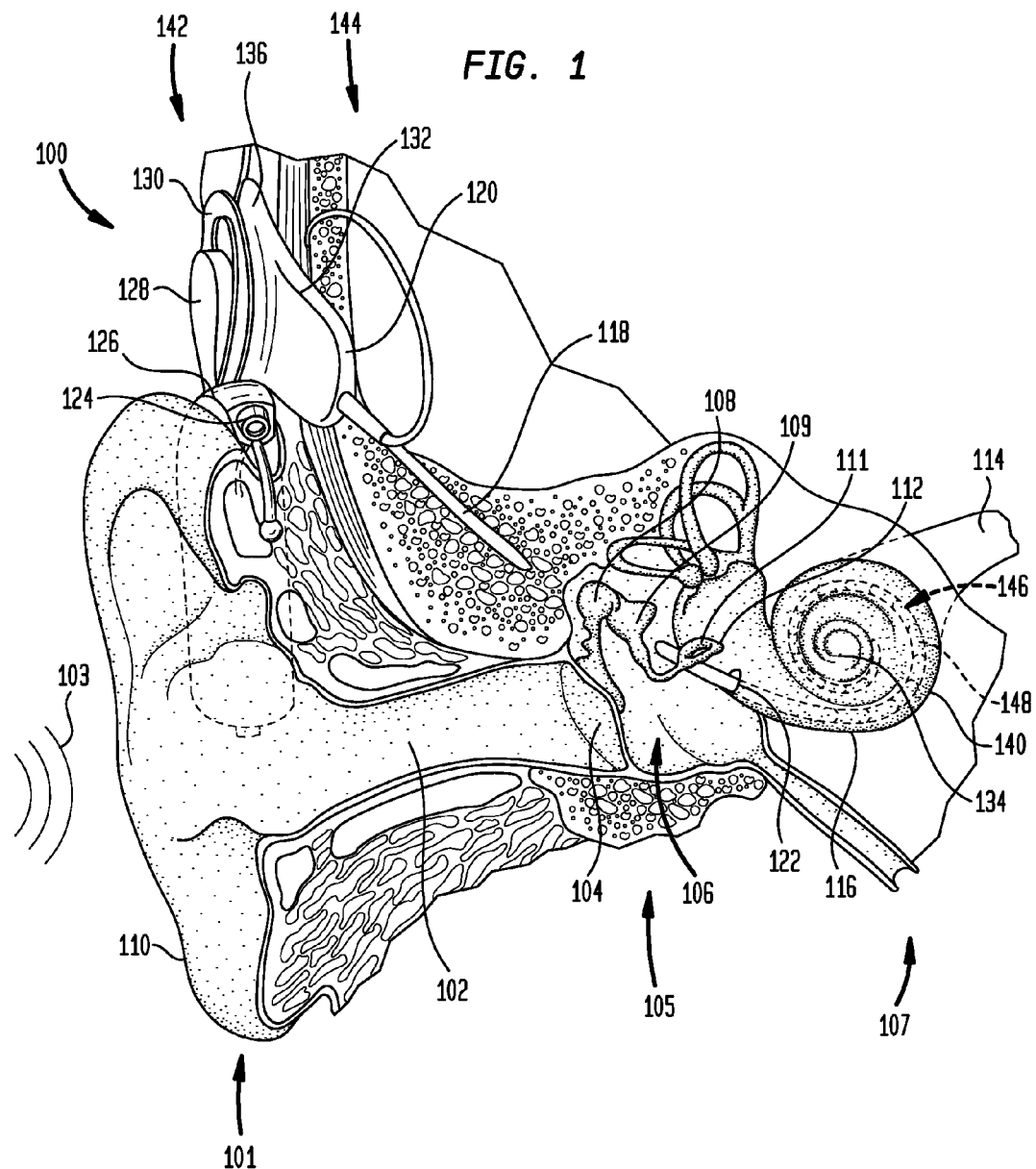
FIG. 1 is a perspective view of an implanted cochlear implant, in accordance with embodiments of the present invention.

FIG. 1 is perspective view of an exemplary medical device having an implantable carrier member, namely a cochlear implant 100. In FIG. 1, cochlear implant 100 is shown implanted in a human cochlea. The relevant components of outer ear 101, middle ear 105 and inner ear 107 are described next below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate. Such vibration sets up waves of fluid motion within cochlea 140. Such fluid motion, in turn, activates tiny hair cells (not shown) that line the inside of cochlea 140. Activation of the hair cells causes appropriate nerve impulses to be transferred through the spiral ganglion cells and auditory nerve 114 to the brain (also not shown), where they are perceived as sound.

Cochlear implant 100 comprises external component assembly 142 which is directly or indirectly attached to the body of the recipient, and an internal component assembly 144 which is temporarily or permanently implanted in the recipient.

External assembly 142 typically comprises one or more audio pickup devices for detecting sound such as microphone 124, a sound processor 126, a power source (not shown), and an external transmitter unit 128. External transmitter unit 128 comprises an external coil 130 and, preferably, a magnet (not shown) secured directly or indirectly to external coil 130. Sound processor 126 processes the electrical signals generated by microphone 124 that is positioned, in the depicted embodiment, by auricle 110 of the recipient. Sound processor 126 generates coded signals, referred to herein as a stimulation data signals, which are provided to external transmitter unit 128 via a cable (not shown).

Internal assembly 144 comprises an internal receiver unit 132, a stimulator unit 120, and a stimulating lead assembly 118. Internal receiver unit 132 comprises an internal transcutaneous transfer coil 136, and preferably, a magnet (also not shown) fixed relative to the internal coil. Internal receiver unit 132 and stimulator unit 120 are hermetically sealed within a biocompatible housing. The internal coil receives power and stimulation data from external coil 130, as noted above. Stimulating lead assembly 118 has a proximal end connected to stimulator unit 120 and extends from stimulator unit 120 to cochlea 140. Stimulating lead assembly 118 is implanted into cochlea 104 via a cochleostomy 122.

Stimulating lead assembly 118 comprises an electrode array 146 disposed at the distal end thereof. Electrode array 146 comprises a plurality of longitudinally-aligned electrodes 148. Stimulation signals generated by stimulator unit 120 are applied by electrode contacts 148 to cochlea 140, thereby stimulating auditory nerve 114.

In some cochlear implants, external coil 130 transmits electrical signals (that is, power and stimulation data) to the internal coil via a radio frequency (RF) link. The internal coil is typically a wire antenna coil comprised of multiple turns of electrically insulated single-strand or multi-strand platinum or gold wire. The electrical insulation of the internal coil is provided by a flexible silicone molding (not shown). In use, implantable receiver unit 132 may be positioned in a recess of the temporal bone adjacent auricle 101 of the recipient.

Any speech coding strategy now or later developed may be implemented by sound processor 126 to convert sound 103 into electrical stimulation signals. For example, sound processor 126 may implement Continuous Interleaved Sampling (CIS), Spectral PEAK Extraction (SPEAK), Advanced Combination Encoders (ACE), Simultaneous Analog Stimulation (SAS), MPS, Paired Pulsatile Sampler (PPS), Quadruple Pulsatile Sampler (QPS), Hybrid Analog Pulsatile (HAPs), n-of-m and HiRes™, developed by Advanced Bionics. SPEAK is a low rate strategy that may operate within the 250-500 Hz range. ACE is a combination of CIS and SPEAK. Examples of such speech strategies are described in U.S. Pat. No. 5,271,397, the entire contents and disclosures of which is hereby incorporated by reference. Other speech coding strategies may be implemented, such as a low rate strategy called Spread of Excitation which is described in U.S. Provisional No. 60/557,675 entitled, "Spread Excitation and MP3 coding Number from Compass UE" filed on Mar. 31, 2004, U.S. Provisional No. 60/616,216 entitled, "Spread of Excitation And Compressed Audible Speech Coding" filed on Oct. 7, 2004, and PCT Application WO 02/17679A1, entitled "Power Efficient Electrical Stimulation," which are hereby incorporated by reference herein.

Cochlear implant 100 may locally store several speech coding strategies, such as in the form of a software program or otherwise, any one of which may be selected depending, for example, on the aural environment. For example, a recipient may choose one strategy for a low noise environment, like a conversation in an enclosed room, and second strategy for a high noise environment, such as on a public street. The programmed speech strategies may be different versions of the same speech strategy, each programmed with different parameters or settings.

Figure 2A:
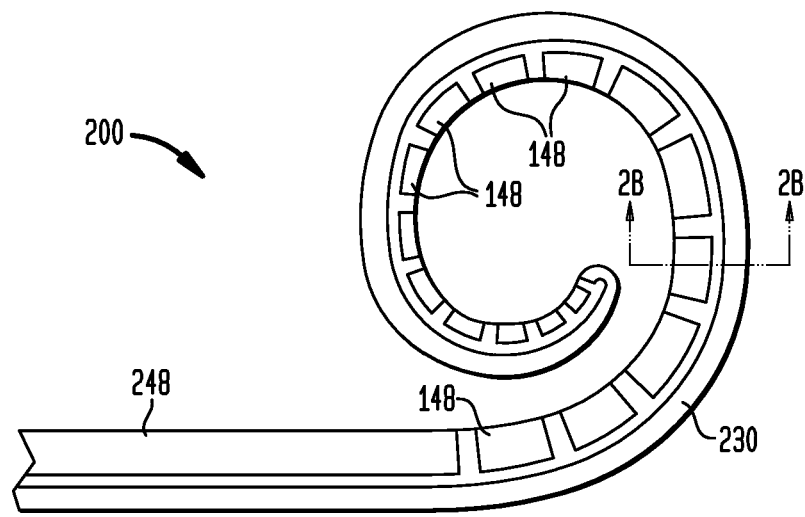
FIG. 2A is a side view of an electrode assembly, in accordance with an embodiment of the present invention.
Figure 2B:
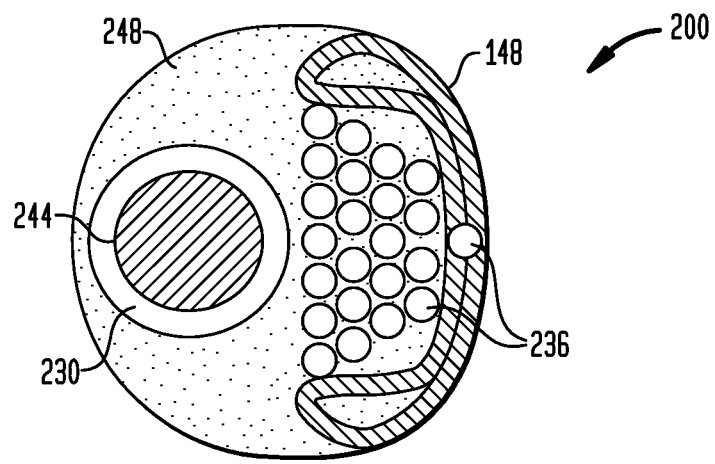
FIG. 2B is a cross-sectional view of an electrode assembly, in accordance with an embodiment of the present invention.

FIGS. 2A and 2B provide simplified views of an embodiment of stimulating lead assembly 118, referred to herein as stimulating lead assembly 200. FIG. 2A is a side view of stimulating lead assembly 200 in its curved orientation. FIG. 2B is a cross-sectional view of stimulating lead assembly 200 taken along section lines 2B-2B of FIG. 2A. As illustrated, stimulating lead assembly 200 comprises a plurality of electrode contacts 148 extending lengthwise along electrode assembly 118 and disposed in a carrier member 248. Carrier member 248 may be manufactured from a suitable material such as silicone, and electrode contacts 148 may be manufactured from a suitable material such as platinum. Stimulating lead assembly 200 may further comprise a lumen 230 through which a stylet 244 may be placed for use in implantation of stimulating lead assembly 200 in the recipient's cochlea.

Each electrode contact 148 may be connected to a wire 236 which extends from the electrode 134 through the stimulating lead assembly 200 to stimulator unit 120. In an embodiment, stimulating lead assembly 200 comprises 22 electrode contacts, although in other embodiments, stimulating lead assembly 200 may comprise any number of electrode contacts. A further description of an exemplary electrode assembly 118 and electrode contacts 148 is provided in U.S. Pat. No. 6,421,569, by Treaba et al., entitled "Cochlear Implant Array of electrode contacts," the entire contents of which are hereby incorporated by reference. Further, in yet other embodiments, stimulating lead assembly 200 may, in addition to electrode contacts, comprise one or more optical contacts for providing optical stimulation to cochlea 140. For example, in an embodiment, optical stimulation and/or electrical stimulation may be provided to encourage the peripheral processes to grow towards the optical contacts in order to improve the application of stimulation by the optical contacts.

Figure 3B:
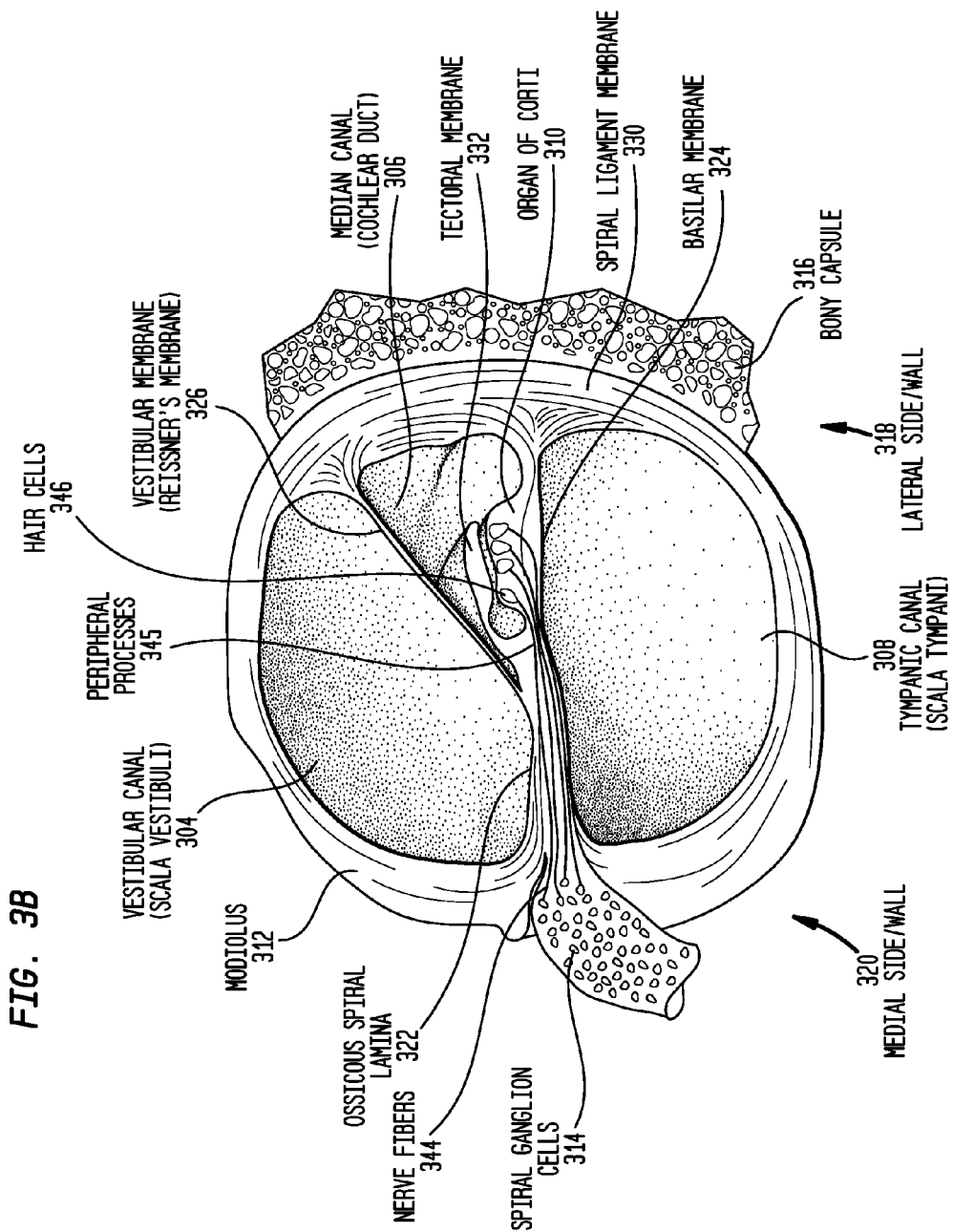
FIG. 3B is a cross-sectional view of one turn of a canal of a cochlea.

Relevant aspects of a human cochlea are described next below with reference to FIGS. 3A and 3B. FIG. 3A is a perspective view of a human cochlea partially cut-away to display the canals of the cochlea. FIG. 3B is a cross-sectional view of one turn of the canals of the cochlea illustrated in FIG. 3A. To facilitate understanding, the following description will reference the cochlea illustrated in FIGS. 3A and 3B as cochlea 140, introduced above with reference to FIG. 1.

Referring to FIG. 3A, cochlea 140 is a conical spiral structure comprising three parallel fluid-filled canals, one or more of which are sometimes referred to as ducts. The canals, collectively and generally referred to herein as canals 302, comprise the tympanic canal 308, also know as the scala tympani 308, the vestibular canal 304, also referred to as the scala vestibule 304, and the median canal 306, also referred to as the cochlear duct 306. Cochlea 140 consists of a conical shaped central axis, the modiolus 312, that forms the inner wall of scala vestibule 304 and scala tympani 308. Tympanic and vestibular canals 308, 304 transmit pressure, while medial canal 306 contains the organ of Corti 310 which detects pressure impulses and responds with electrical impulses which travel along the auditory nerve fibers 114 to the brain (not shown).

Referring now to FIG. 3B, separating canals 302 of cochlear 140 are various membranes and other tissue. The Ossicous spiral lamina 322 projects from modiolus 312 to separate scala vestibuli 304 from scala tympani 308. Toward lateral side 318 of scala tympani 308, a basilar membrane 324 separates scala tympani 308 from cochlear duct 306. Similarly, toward lateral side 318 of scala vestibuli 304, a vestibular membrane 326, also referred to as the Reissner's membrane 326, separates scala vestibuli 304 from cochlear duct 306. The modiolar bony wall (also referred to as the osseus surface) of the scala tympani 308 has small canals, referred to as canaliculi perforantes (not shown), therein. Further, the top of the bony wall of the scala tympani 308, consisting for the largest part out of quiescent osteoblasts, is covered by a soft tissue (not shown).

The fluid in tympanic and vestibular canals 308, 304, referred to as perilymph, has different properties than that of the fluid which fills cochlear duct 306 and surrounds organ of Corti 310, referred to as endolymph. Sound entering auricle 110 causes pressure changes in cochlea 140 to travel through the fluid-filled tympanic and vestibular canals 308, 304. As noted, organ of Corti 310 is situated on basilar membrane 324 in cochlear duct 306. It contains rows of 16,000-20,000 hair cells 346 which protrude from its surface. Above them is the tectoral membrane 332 which moves in response to pressure variations in the fluid-filled tympanic and vestibular canals 308, 304.

Small relative movements of the layers of membrane 332 are sufficient to cause, in a person with normal hearing, the hair cells 346 to send a voltage pulse or action potential to the associated spiral ganglion cell 314. Spiral ganglion cells 314, also referred to as spiral ganglion neurons, comprise nerve fibers 344, embedded within spiral lamina 322, that are connected to the peripheral processes 345 (also referred to as dendrites) of the neuron 314. Nerve fibers 344 are also sometimes referred to as axons 344. Impulses generated by the hair cells 346 are received by the peripheral processes 345 and travel through nerve fibers or axons 344 to the corresponding cell body of the spiral ganglion cells 314. These impulses then travel via to the auditory areas of the brain for processing.

The place along basilar membrane 324 where maximum excitation of the hair cells 346 occurs determines the perception of pitch and loudness according to the place theory. Due to this anatomical arrangement, cochlea 140 has characteristically been referred to as being "tonotopically mapped." This property of cochlea 140 has traditionally been exploited by longitudinally positioning electrodes 148 along carrier member 118 to deliver to a selected region within scala tympani 308 a stimulating signal within a predetermined frequency range.

Portions of cochlea 140 are encased in a bony capsule 216. Referring to FIG. 3B, cochlear bony capsule 316 resides on lateral side 318 (the right side as drawn in FIG. 3B), of cochlea 140. Spiral ganglion cells 314 reside on the opposing medial side 320 (the left side as drawn in FIG. 3B) of cochlea 140. A spiral ligament membrane 330 is located between lateral side 318 of scala tympani 308 and bony capsule 316, and between lateral side 318 of cochlear duct 306 and bony capsule 316. Spiral ligament 330 also typically extends around at least a portion of lateral side 318 of scala vestibuli 304.

Figure 4:
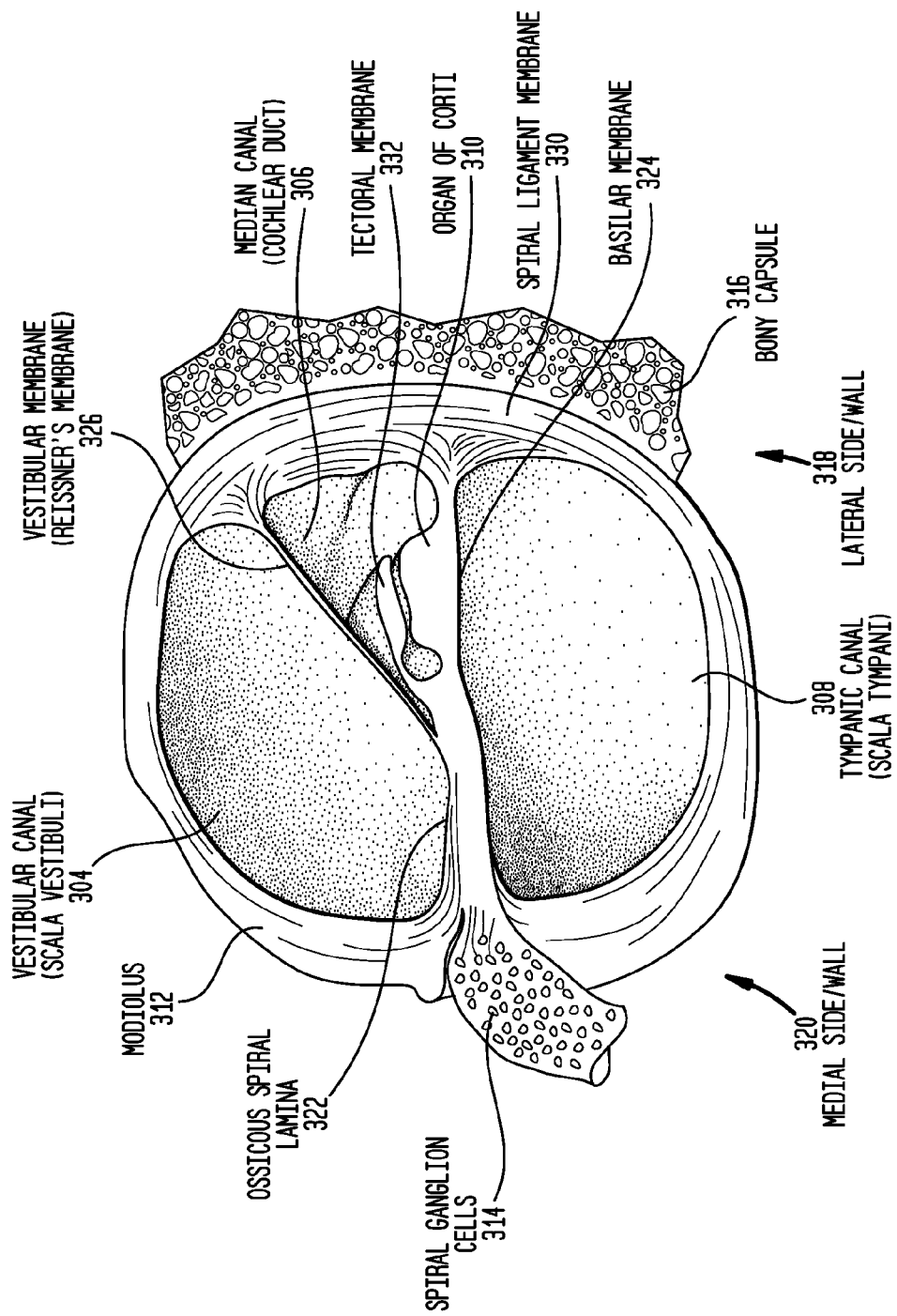
FIG. 4 is a cross-sectional view of one turn of a canal of cochlea in which hair cells, peripheral processes, and nerve fibers have deteriorated.

In sensorial hearing loss, there is often a loss of hair cells 346. This results in peripheral processes 345 shrinking back towards spiral ganglion cell bodies. The death of hair cells 346 thus results in the eventual loss of peripheral processes 345. FIG. 4 illustrates a cross-sectional view of one turn of the cochlea in which the hair cells have degraded, leading to sensorineural deafness. As illustrated, peripheral processes 345 have also dramatically deteriorated, and even some nerve fibers 344 have degraded.

Figure 5:
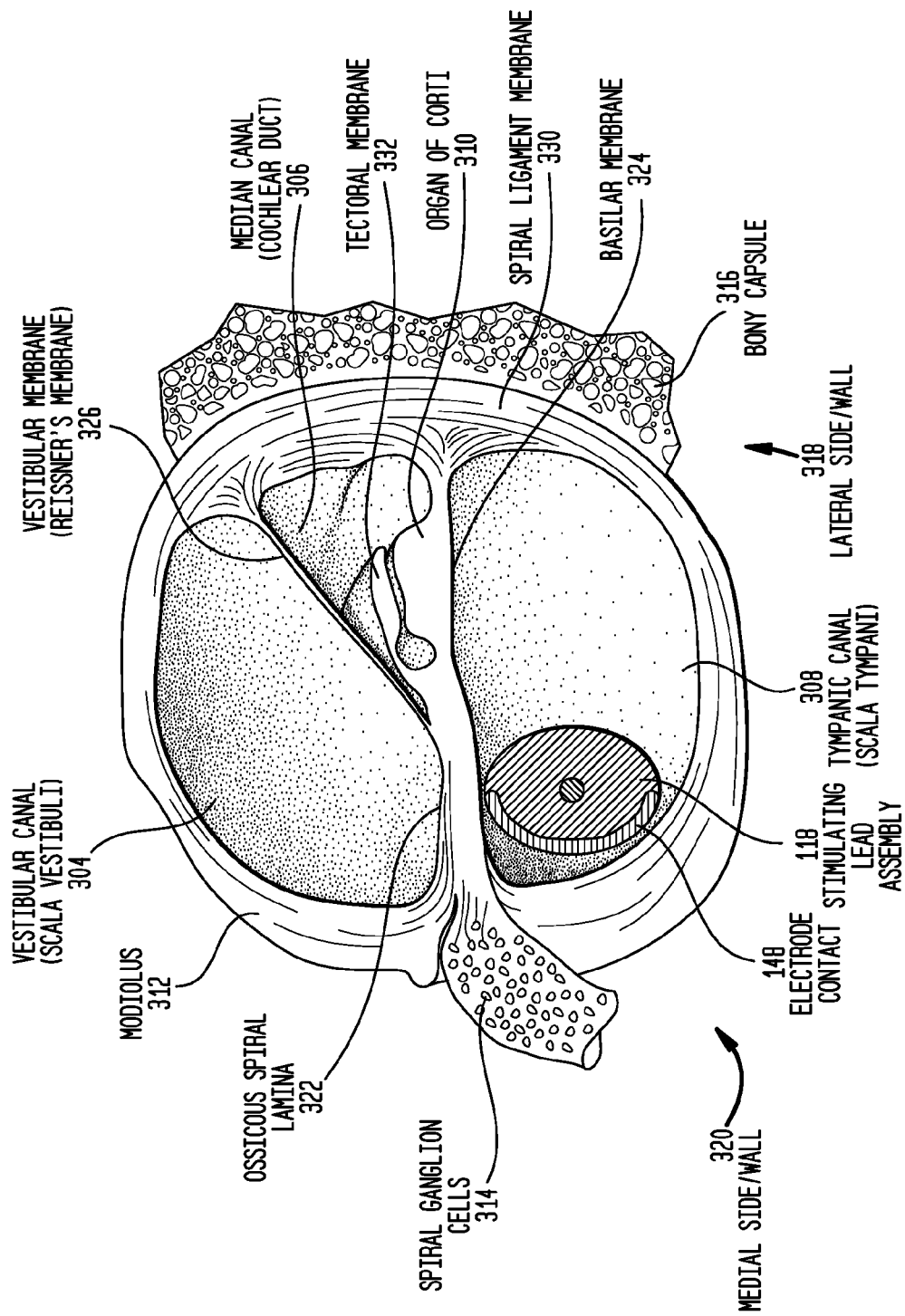
FIG. 5 is a cross-sectional view of one turn of a canal of cochlea in which a electrode assembly inserted therein, in accordance with an embodiment of the present invention.

FIG. 5 illustrates a cross-section view of the cochlea 140 of FIG. 4 in which a stimulating lead assembly has been inserted into scala tympani 308 of the cochlea, such as was discussed above with reference to FIG. 1. As shown, electrode contacts 148 are oriented such that they are directed towards spiral ganglion cells 314 and positioned such that the electrode contacts 148 are in close proximity to modiolus 312.

The loss of peripheral processes 345 results in less peripheral processes 345 for the electrode contacts 148 to stimulate. Thus, when stimulation is applied by a stimulating lead assembly 118, the stimulation may result in a predominance of stimulating the cell bodies of spiral ganglion cells 314 rather than the stimulation being shared with the peripheral processes 345. This may result in the cochlear implant system being able to achieve potentially less frequency distinction and higher threshold current levels (also known as T-levels). For example, although positioned near the modiolus 312, the electrode contacts 148 are still located somewhat distant from the spiral ganglion cells 314 and the stimulation travels via the perilymph which has relatively low impedance and tends to spread the stimulation. Thus, due to the spread of stimulation from the electrode contacts 148, nearby electrode contacts 148 may stimulate overlapping populations of the spiral ganglion cells 314, thus resulting in a decrease in the ability of cochlear implant 100 to finely distinguish frequencies. Further, because the stimulation travels further and is predominantly received by the spiral ganglion cells 314, the amount of current needed for sound to be perceived by the recipient (i.e., the threshold current) is increased. Accordingly, this loss of peripheral processes may make it more difficult to provide stimulation via a cochlear implant to provide a satisfactory level of hearing performance for the recipient.

Figure 6:
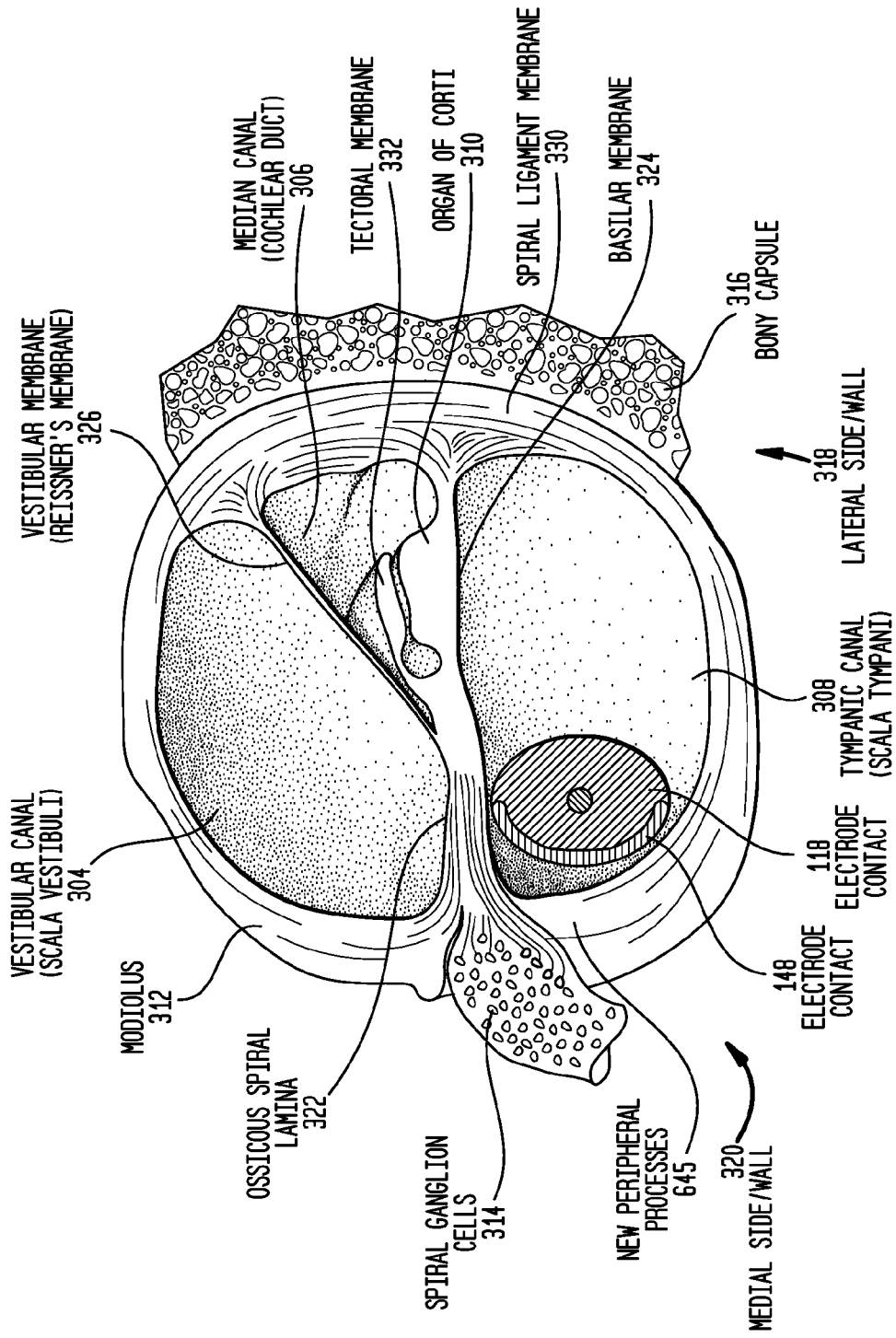
FIG. 6 is a cross-sectional view of one turn of a canal of cochlea in which new peripheral processes have grown, in accordance with an embodiment of the present invention.

As will be discussed in more detail below, in an embodiment, a method is employed that causes the spiral ganglion cells 314 to sprout new peripheral processes that are directed towards, for example, electrode contacts 148 of stimulating lead assembly 118, such as illustrated in FIG. 6. Directing the growth of peripheral processes 645 towards the electrode contacts 148 results in the delivered stimulation current having less distance to travel before being received by spiral ganglion cells 314. Thus, the threshold current level (i.e., the minimum current level that results in sound being perceived by the recipient) for the electrode contacts 148 is reduced. Thus because reduced current levels may be used to achieve sound perception by the recipient, the stimulation spread from the electrode contacts 148 is less. This accordingly may result in the cochlear implant being able to achieve finer frequency distinction as well as a greater pitch discrepancy.

As discussed in more detail below, an embodiment uses a two step process that involves first applying neural growth factor(s) to promote the sprouting of new peripheral processes 645. Subsequent to or concurrent with application of the growth factor, electric fields are generated that direct the growth of the peripheral processes 645 towards the electrode contacts 148.

FIG. 7 illustrates a simplified diagram of an exemplary method for encouraging the growth of peripheral processes towards an electrode contact, in accordance with an embodiment of the invention. FIG. 7 will be discussed with reference to FIGS. 1, 2 and 6.

Initially, a surgeon implants a stimulating lead assembly 118 into the cochlea 140 of the recipient at block 702. Conventional surgical means may be used for implantation of stimulating lead assembly 118 as well as the other internal components 144 of cochlear implant 100.

After allowing the recipient to heal from the implantation surgery, at block 704, a growth factor (GF) may be applied to cause the spiral ganglion cells 314 to sprout new peripheral processes 645. This may be accomplished by, for example, acutely applying a GF. As used herein, the term "acute" refers to applying the growth factor for a limited amount of time and/or to a localized region. For example, in an embodiment, the growth factor may be applied for a period of less than 28 days. Further, in an embodiment, once the spiral ganglion cells 314 have sprouted new peripheral processes 645, the application of GFs is terminated. Additionally, in an embodiment, the growth factor is applied to a localized area, such as, for example, to the modiolar wall of the cochlea.

Various types of GFs may be used to promote the spiral ganglion cells to sprout peripheral processes. For example, in an embodiment, a neurotrophin may be used as the GF, such as, for example a neural growth factor (NGF), a Brain derived neurotrophic factor (BDNF), neurotrophin 3 (NT-3), or neurotrophin 4/5 (NT4/5). Or for example, a glial cell line-derived neurotrophic factor (GDFN) family ligand (GFL) may be used, as the GF, such as GDFN neurtrin (NRTN), artemin (ARTN, and/or persephine (PSPN). Or, in another embodiment, the GF may be an interleukine (IL)-6-type cykotine, such as IL-6, IL-11, leukameia inhibitory factor (LIF), oncostatin M (OSM), ciliary neurotrophic factor, cardiotrophin-1, and/or a cardiotrophin-like cytokine. Or, in yet another embodiment a GF from the fibroblast GF (FGF) family, which contains 23 members in the human family may be used, such as, for example, FGF1 through FGF23.

As noted, the modiolar bony wall (i.e., the wall nearest modiolus 312) of scala tympani 308 has small canals therein, and the top of the bony wall of the scala tympani 308 is covered by a soft tissue. However, this soft tissue does not completely cover the bony wall. This provides a fluidic communications channel between the scala tympani 308 and the spiral ganglion cells 314. Thus, a GF applied in the region of the bony wall of scala tympani 308 near spiral ganglion cells 314 may traverse this fluidic communications channel such that the GF may promote the sprouting of peripheral processes 645 by spiral ganglion cells 314.

Various techniques may be used to apply the GFs to spiral ganglion cells 314, such as the drug delivery techniques discussed in International Patent Application No. PCT/AU2003/001584, which is hereby incorporated by reference herein. For example, referring to FIG. 2, in an embodiment the stimulating lead assembly 200 may be coated with a GF. In one such embodiment, the GF may be suspended in a dissolving polymer used to coat the stimulating lead assembly 200 such that when implanted within cochlea 140, the polymer dissolves thus releasing the GF which may traverse the above-discussed fluidic communication channel to the spiral ganglion cells 314.

The GF may be applied to the stimulating lead assembly 118 such that an almost equal concentration of GF is created next to the modiolar wall of the scala tympani 308. In one embodiment, the stimulating lead assembly 200 may be coated with the GF by dipping the stimulating lead assembly 200 into a dissolving polymer in which the GF is suspended, for example, at the time of manufacture of the stimulating lead assembly 200, or immediately prior to implantation of the stimulating lead assembly 200.

Or, for example, in other embodiments, the GF may be applied by other means, such as by direct infusion of the GF into the scala tympani, scala vestibuli, or scala media. Or, for example, the GF may be delivered via the round window of the cochlea. Or, in yet another embodiment, the GF may be administered by acute injection of the GF into the scala tympani. Alternatively, gene-based and/or cell based therapies may be used for applying the growth factor. Or, for example, a pump mechanism may be used, such as described in the above-referenced International Patent Application No. PCT/

AU2003/001584, to administer the growth factor, for example, over a period of between 7 and 28 days.

Or, in yet another embodiment, a durable (non-degradable) substrate, such, as silicone rubber, that either allows for dissolution of the drug (e.g., fluid enters the drug and dissolves the drug) or a drug accessible surface. For example, referring back to FIG. 2, the carrier member 248 may be manufactured from a porous silicone, where the pores have disposed therein a bioactive substance in which the GF is suspended. Or, for example, the electrode contacts may be formed from a biocompatible porous platinum material in which the bioactive substance with the GF is disposed within the pores.

After or concurrent with administering the GF, a directional stimulation may be applied, at block 706, for directing the growth of the new peripheral processes 645 towards the electrode contacts 148. This may be accomplished by generating an electric field in a direction from the spiral ganglion cells 314 towards the electrode contacts 148. One way for generating such an electric field is for the electrode contacts to apply a direct current (DC). The application of DC to cochlea 140, however, may result in the undesirable accumulation of a charge within cochlea 140, and thus the use of DC current is generally undesirable. As such, in applying stimulation for inducing a hearing sensation, the cochlear implant generally uses biphasic pulses to achieve charge recovery and help avoid damage to the electrode contact and toxic electrochemical by-products.

In an embodiment, stimulation with a zero net DC and a non-zero net electric field is provided by harnessing the non-linear properties of the electrode/tissue interface. For example, in one embodiment, cochlear implant 100 briefly applies a larger voltage with a first polarity between two selected electrode contacts 148 of stimulating lead assembly 118 for a first period of time, and then applies a smaller voltage of the opposite polarity for a second period of time that is greater than the first period of time. This is then repeated at a suitable frequency, e.g., minutes per phase. Stimulation which promotes the growth of a peripheral process in a particular direction is referred to herein as "directional stimulation." Additionally, as used herein the term "non-zero net electric field" refers to an electrically charged region exerting an electrical force in a particular direction. Further as used herein, the term "net zero DC" signal refers to a signal that is substantially charge balanced. For example, a recipient may be able to tolerate a long term non-zero pulse of 100 nano amps. Thus, as used herein, the term "net zero DC" includes non-net-zero pulses where the accumulated charge of the pulses stays under this 100 nano amp value.

Referring back to FIG. 1, cochlear implant 100 may generate the non-zero electric field with zero net DC stimulation signal by applying sub-threshold stimulation using electrode contacts 148 of cochlear implant 100. For example, in an embodiment, sound processor 126 may be programmed to generate stimulation data signals for the applying the stimulation, which are provided to external transmitter unit 128 via a cable (not shown). These data signals are then received by internal receiver unit 132 where they are provided to stimulator unit 120, which then applies the stimulation via the electrode contacts 148 of stimulating lead assembly 118 to generate the non-zero net electric field with zero net DC.

FIG. 8 illustrates one exemplary embodiment of a stimulation waveform 800 that may be used for directing the growth of the peripheral processes 645, in accordance with an embodiment. As shown, the exemplary stimulation waveform 800 has a net zero DC, while still achieving an electric field in the desired direction (i.e., from the spiral ganglion cells 314 towards electrode contact 148). As shown, the waveform comprises a first positive pulse 802 followed by negative pulse 806. The positive pulse 802 has a large amplitude over a short period of time, while the negative pulse 806 has a lower amplitude over a larger period of time. These two pulses 802 and 806 may be charged balanced such that charge is not built up within cochlea 140 (i.e., the waveform has an approximately zero net DC (i.e., the waveform is substantially charge balanced) and a non-zero net electric field).

The magnitudes of the positive and negative pulses 802 and 806 may be selected such that the pulses are sub-threshold (i.e., the magnitude of the pulses are below the current level for which a hearing sensation would be induced in the recipient). Exemplary values for the positive pulse 802 may be for example over a range of a current amplitude of 10 micro-amps over a duration of 25 micro-seconds up to a amplitude of 1.75 milli-amps over a duration of 200 micro-seconds. Further, as illustrated there may be a short time gap 804 between the application of the positive and negative pulses that is much shorter than the pulse durations. The magnitude and duration of the negative pulse 806 may be selected so that it is as long and low as possible, but high enough to achieve electrochemical balance.

The amplitude and duration of the positive pulse 802 may be selected such that the positive pulses are sufficient to direct growth of the peripheral processes towards the electrode contact(s). And, the amplitude and duration of the negative pulse 806 may be selected so as to reduce repulsion of the growth of the peripheral processes towards the electrode contact(s). In an embodiment, the amplitude of the positive pulse 802 (phase 1) may be selected such that the system generates an electric field near the neural tissue having a strength exceeding a threshold field strength for directing the growth of the peripheral processes. The amplitude of the negative pulse 806 (phase 2) may be selected such that the generated electric field will have a strength below this threshold field strength. Thus, the positive pulse 802 will be more likely to direct (e.g., attract) the growth of the peripheral processes than the negative pulse. Current literature indicates that the threshold field strength for directing the growth of peripheral processes is about or equal to 7 mV/mm.

In an embodiment, the stimulation waveform may be applied as a constant repeating stimulation pattern that is repeated over a period of weeks to about 1 month to promote the growth of the peripheral processes 645 towards the electrode contacts 148. For example, in one embodiment, the stimulation pattern may be applied for a period of less than or equal to 28 days, or, for example, less than or equal to 21 days.

After the peripheral processes 645 are grown, the stimulation for directing the growth of the peripheral processes 645 may be terminated. Then, at block 708, the stimulating lead assembly may apply stimulation for the purposes of inducing hearing by the recipient, referred to herein as "auditory stimulation." Using a stimulating lead assembly 118 to induce a hearing sensation is well known to those of skill in the art and as such is not describe further herein.

In directing the growth of the peripheral processes, the directional stimulation may be applied in a number of different ways. For example, in an embodiment, no traditional stimulation (i.e., stimulation for inducing a hearing sensation) is applied for an initial time period (e.g., 2 weeks), and only the directional stimulation is applied. Or, in another embodiment, the direction stimulation is only applied at night (e.g., when the recipient is sleeping), and traditional stimulation is applied during the day (e.g., when the recipient is awake). Or, for example, in an embodiment, directional stimulation and traditional stimulation may be applied concurrently.

Further, rather than applying the electric field concurrent with or subsequent to the application of the growth factor, in an embodiment, the growth factor may be applied for a period of time and then stopped, then only the electric field is applied, after which the growth factor is applied again, and so on. That is the growth factor and electric field may be applied in some repetitive fashion, such that the growth factor is applied at a number of times of limited duration.

In the above-discussed embodiments, directional stimulation is applied using a waveform that has zero net DC and a non-zero net electric field. In another embodiment, directional stimulation may be applied using an ion switch, such as described in Australian Provisional Application No. 2008904594, entitled "Ion Switch for Neural Stimulation," and Australian Patent Application No. 2009222439, entitled "Method and Circuitry for Measurement and Control of Stimulation Current," filed Sep. 28, 2009, each of which is incorporated by reference herein.

Figure 9A:
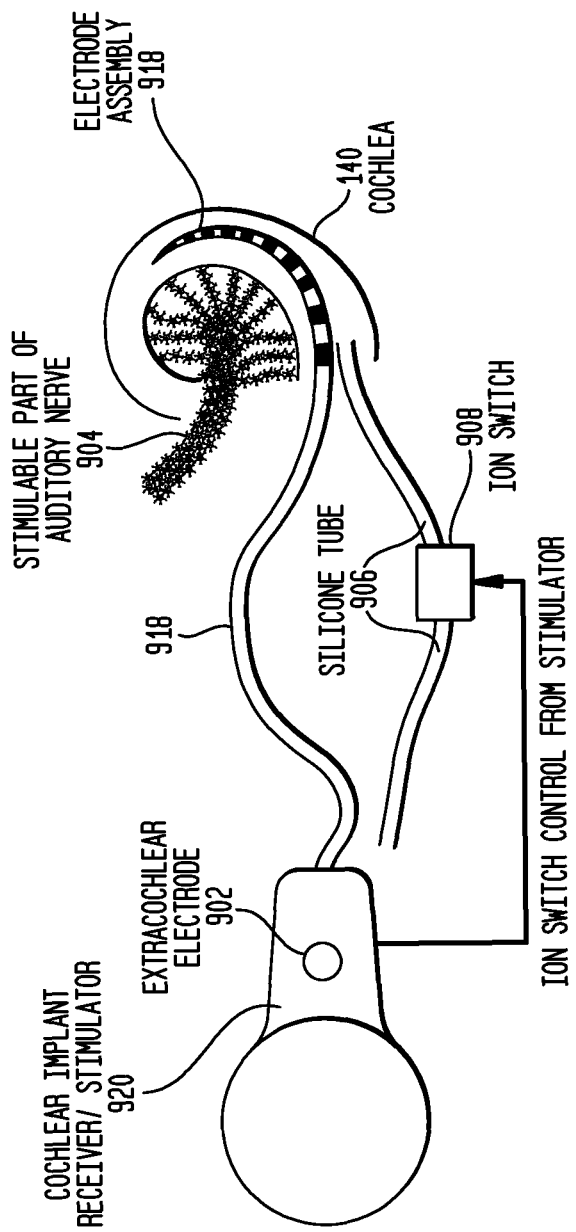
FIG. 9A is a conceptual diagram illustrating an embodiment employing an ion switch, in accordance with an embodiment of the invention.

FIG. 9A illustrates a conceptual diagram of a cochlear implant 900 using an ion switch. For simplicity, only the internal assembly of cochlear implant 900 is illustrated, and the external assembly may be, for example, similar or identical to the external assembly of cochlear implant 100 discussed above with reference to FIG. 1. As illustrated, cochlear implant 900 may comprise a receiver/stimulator unit 920, which may, for example, be a combined unit including an internal receiving unit and a stimulator unit similar or identical to the internal receiving unit 132 and stimulator unit 120 discussed above with reference to FIG. 1.

Additionally, receiver/stimulator unit 920 may comprise an extracochlear electrode 902, which is commonly used in applying monopolar stimulation. Stimulator/receiver unit 920 may be connected to a stimulating lead assembly 918 comprising one or more electrode contacts 948 implanted in the recipients cochlea 140. Stimulating lead assembly 918 may be, for example, configured for delivering a growth factor to the recipient's cochlea, such as discussed above (e.g., stimulating lead assembly may be coated with a polymer in which the growth factor is suspended, may comprise pores in which the growth factor is disposed, etc.).

Cochlear implant 900 may also comprise a silicone insulated tube 906 with an ion switch 908 positioned, for example, between the two ends of the insulated tubing 906. Ion switch 908 may be connected to receiver/stimulator unit 920, which may control the operation of ion switch 906. The ends of silicone tubing 906 may be positioned such that the tube 906 provides a low impedance path around the stimulated neural structures 904 when ion switch 908 is closed (i.e., low impedance). For example, as shown, one end of the silicone tube 906 is positioned within cochlea 140 and the other end is positioned near extra-cochlea electrode 902. Thus, in the present embodiment, ion switch 906 may be opened and closed to allow charge balanced stimuli to be passed across the electrode/tissue interface while allowing non-charge balanced stimuli to flow across the auditory nerve 904.

FIG. 9B illustrates the conceptual flow of stimulation during operation of the cochlear implant 900 of FIG. 9A, in accordance with an embodiment of the present invention. In a first phase of the directional stimulation, the ion switch 908 is open (i.e., high impendence) and receiver/stimulator unit 920 delivers a current stimulus from the extracochlear electrode 902 to one or more intra-cochlear electrode contacts 948 of the stimulating lead assembly 118. This current passes through the auditory nerve 904 and is received by the intra-cochlear electrode contacts 948, which then returns the current to receiver/stimulator unit 920. This stimulation for this phase may be the same, or similar to, monopolar stimulation applied using convention cochlear implants. In such an example, the electrode contacts 948 act as a cathode, which may attract the growth of the peripheral processes.

During the second phase, receiver/stimulator unit 902 closes ion switch 908 (i.e., low impendence) and sends a stimulation pulse. The current applied from the intra-cochlear electrode contacts to the extracochlear electrode during this second phase may be identical to the current applied during the first phase, but of opposite polarity. As a result of ion switch 908 being closed (low impedance) during this second phase, current in this second phase does not flow across the auditory nerve 904 and therefore does not return the neural structures to their state prior to phase 1. Rather, the current flows from the receiver/stimulator unit 920 to stimulating lead assembly 918, into silicone tube 906, to extra-cochlea electrode 902, and then back to receiver/stimulator unit 920. Thus, a net zero DC may achieved at the intra-cochlear electrode contact surface and the extracochlear electrode surface, while still applying a non-zero net electric field to the neural structures. It should be appreciated that if the switch 908 is closed in the first phase and open in the second phase, a net electric field across the neural structures in the opposite direction may be achieved. Thus, a system such as described above with reference to FIG. 9, may be used to direct the growth of peripheral processes in a desired direction, such as towards the electrode contacts.

Although the embodiment of FIG. 9B was discussed with reference to the current flow going from the extracochlea to the intra-cochlea electrode contacts in phase 1, and traveling via the silicone tube in phase 2, it should be understood that in other embodiments it may be desirable to reverse the phases such that current flows from the extracochlea electrode to the intra-cochlea electrode contacts via the silicone tube in phase 1, and from the intra-cochlea electrode contacts to the extra-cochlea contact via the auditory nerve in phase 2.

Although the above description was discussed with reference to using electrical stimulation for generating the directional stimulation, in other embodiments other types of stimulation, such as optical stimulation may be used. Optical stimulation may provide the benefit of being able to provide the directional stimulation without charge balance issues.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All patents and publications discussed herein are incorporated in their entirety by reference thereto.

What is claimed is:

1. A method for directing the growth of neural peripheral processes comprising: applying to a plurality of neurons a growth factor which promotes growth of the peripheral processes by the neurons; and applying to the neurons an electric field having characteristics which encourage the growth of the peripheral processes in a desired direction, wherein the electric field includes a biphasic stimulation signal having a first phase that passes through the plurality of neurons and a second phase that bypasses the plurality of neurons.

2. The method of claim 1, wherein a stimulating assembly is implanted within a cochlea of the recipient, and further wherein the application of the electric field is applied by a first one or more electrode contacts of the stimulating assembly and further wherein the desired direction of growth of the peripheral processes is towards a second one or more electrode contacts of the stimulating assembly.

3. The method of claim 2, wherein applying the electric field to the neurons comprises:
delivering via the first electrode contacts the biphasic stimulation signal.

4. The method of claim 3, wherein the first phase of the biphasic stimulation signal is a positive phase having an amplitude and duration sufficient to provoke said directed growth, and wherein the second phase of the biphasic stimulation pulse has an amplitude and duration sufficient to not cause a repulsion and to provide a charge-balanced biphasic stimulation signal.

5. The method of claim 4, wherein the net charged by the first and second phases over the first and second durations is substantially zero.

6. The method of claim 3, wherein the action of applying to the neurons an electric field includes:
wherein the first phase of the biphasic stimulation signal is a positive phase having a strength exceeding a threshold field strength for directing the growth of the peripheral process in the desired direction, and
wherein the second phase is a negative phase having a strength below the threshold field strength.

7. The method of claim 6, wherein the first phase directs more growth of the peripheral process than the second phase.

8. The method of claim 1, wherein the growth factor is applied over a period of less than or equal to 28 days.

9. The method of claim 8, wherein the growth factor is applied over a period of less than or equal to 21 days.

10. The method of claim 1, wherein the applying the growth factor comprises applying the growth factor via a stimulating lead assembly, and wherein the stimulating lead assembly comprises a dissolving polymer in which the growth factor is suspended that dissolves to release the growth factor.

11. The method of claim 1, wherein:
the first phase of the biphasic stimulation signal is delivered from an extracochlear electrode to one or more intra-cochlear electrode contacts of an electrode assembly implanted in a cochlea;
the second phase of the biphasic stimulation signal is delivered from the intra-cochlear electrode contacts to the extracochlear electrode via an electrical conduit with an end located in the cochlea proximate the electrode assembly, the electrical conduit being separate from a stimulating lead assembly of which the electrode contacts are a part of;
an impedance of the electrical conduit is at a heightened level during the first phase, thereby discouraging flow of the stimulation signal via the electrical conduit; and
an impedance of the electrical conduit is at a lowered level during the second phase, thereby encouraging flow of the stimulation signal via the electrical conduit.

12. A system for directing the growth of neural peripheral processes comprising: a stimulating lead assembly comprising one or more electrode contacts, wherein the stimulating lead assembly is configured to apply a growth factor to promote the growth of peripheral processes by a plurality of neurons;
a sound processor configured to generate one or more stimulation data signals; and
a stimulator unit configured to apply an electric field to a cochlea of a recipient in accordance with the one or more stimulation data signals, wherein the electric field has characteristics which encourage the growth of the peripheral processes in a desired direction,
wherein the electric field includes a biphasic stimulation signal having a first phase that passes through the plurality of neurons and a second phase that bypasses the plurality of neurons.

13. The system of claim 12, wherein the stimulation data signals specify an electric field to be applied by the electrode contact using a waveform wherein the first phase has a first polarity and the second phase has an opposite polarity.

14. The system of claim 13, wherein a current level of the first phase is greater than a current level of the second phase and wherein a duration of the first phase is less than a duration of the second phase.

15. The system of claim 14, wherein the net charge of the first and second phases over the first and second durations is substantially zero.

16. The system of claim 12, wherein:
the first phase of the biphasic stimulation signal is a positive phase having a strength exceeding a threshold field strength for directing the growth of the peripheral process in the desired direction; and
the second phase is a negative phase having a strength below the threshold field strength.

17. The system of claim 16, wherein the first phase directs more growth of the peripheral process than the second phase.

18. The system of claim 12, wherein:
the stimulating lead assembly includes an electrode assembly configured to be inserted inside a cochlea;
the system includes an electrical conduit with an end configured to be located in the cochlea proximate the electrode assembly, the electrical conduit being separate from the stimulating lead assembly;
the system is configured to deliver the first phase of the biphasic stimulation signal from an extracochlear electrode to one or more intra-cochlear electrode contacts of the electrode assembly while the electrode assembly is implanted in a cochlea;
the system is configured to deliver the second phase of the biphasic stimulation signal from the intra-cochlear electrode contacts to the extracochlear electrode via the electrical conduit while the end is located in the cochlea proximate the electrode assembly;
the system is configured to set an impedance of the electrical conduit such that the impedance is at a heightened level during the first phase, thereby discouraging flow of the stimulation signal via the electrical conduit; and
the system is configured to set an impedance of the electrical conduit such that the impedance is at a lowered level during the second phase, thereby encouraging flow of the stimulation signal via the electrical conduit.

19. A system for directing the growth of neural peripheral processes comprising:
means for applying to a plurality of neurons a growth factor which promotes the growth of peripheral processes by the neurons; and
means for applying to the neurons an electric field having characteristics which encourage the growth of the peripheral processes in a desired direction,
wherein the electric field includes a biphasic stimulation signal having a first phase that passes through the plurality of neurons and a second phase that bypasses the plurality of neurons.

20. The system of claim 19, wherein the means for applying an electric field is for implantation at least partially within a cochlea of a recipient.

21. The system of claim 19, wherein the means for applying the electric field is further for applying the electrode field using a waveform wherein the first phase has a first polarity and the second phase has an opposite polarity.

22. The system of claim 21, wherein a current level of the first phase is greater than a current level of the second phase and wherein a duration of the first phase is less than a duration of the second phase.

23. The method of claim 22, wherein the net charge by the first and second phases over the first and second durations is substantially zero.

24. The system of claim 19, wherein:
the first phase of the biphasic stimulation signal is a positive phase having a strength exceeding a threshold field strength for directing the growth of the peripheral process in the desired direction; and
the second phase is a negative phase having a strength below the threshold field strength.

25. The system of claim 24, wherein the first phase directs more growth of the peripheral process than the second phase.

26. The system of claim 19, wherein:
the means for applying to the neurons an electric field includes an electrode assembly configured to be inserted inside a cochlea;
the system includes a means for conducting electricity with an end configured to be located in the cochlea proximate the electrode assembly, the means for conducting electricity being separate from a stimulating lead assembly of which the electrode assembly is a part of;
the system is configured to deliver the first phase of the biphasic stimulation signal from an extracochlear electrode to one or more intra-cochlear electrode contacts of the electrode assembly while the electrode assembly is implanted in a cochlea;
the system is configured to deliver the second phase of the biphasic stimulation signal from the intra-cochlear electrode contacts to the extracochlear electrode via the means for conducting electricity while the end is located in the cochlea proximate the electrode assembly;
the system is configured to set an impedance of the means for conducting electricity such that the impedance is at a heightened level during the first phase, thereby discouraging flow of the stimulation signal via the means for conducting electricity; and
the system is configured to set an impedance of the means for conducting electricity such that the impedance is at a lowered level during the second phase, thereby encouraging flow of the stimulation signal via the means for conducting electricity.

* * * * *